United States Patent [19]

Ricard

[11] Patent Number: 4,678,669

[45] Date of Patent: Jul. 7, 1987

[54] METHOD OF USING IMMUNIZING COMMENSALS

[75] Inventor: Jacques J. L. Ricard, Sigtuna, Sweden

[73] Assignees: Suoma Ricard; Thomas Ricard, both of Sigtuna, Sweden

[21] Appl. No.: 576,171

[22] Filed: Feb. 2, 1984

Related U.S. Application Data

[63] Continuation of Ser. No. 269,765, Jun. 3, 1981, abandoned, which is a continuation-in-part of Ser. No. 76,061, Sep. 17, 1979, abandoned, which is a continuation-in-part of Ser. No. 883,272, Mar. 3, 1978, abandoned, which is a continuation-in-part of Ser. No. 722,767, Sep. 13, 1976, abandoned, which is a continuation-in-part of Ser. No. 593,355, Jul. 7, 1975, abandoned, which is a continuation-in-part of Ser. No. 489,874, Jul. 18, 1974, abandoned, which is a continuation of Ser. No. 32,281, Apr. 27, 1970, abandoned.

[30] Foreign Application Priority Data

| Apr. 29, 1969 | [GB] | United Kingdom | 21834/69 |
| Mar. 3, 1977 | [FR] | France | 77 06300 |
| Sep. 22, 1978 | [FR] | France | 78 27197 |

[51] Int. Cl.$^4$ ............ A01N 63/00; A01N 63/02; A61K 37/00
[52] U.S. Cl. ............................................ 424/93; 47/58
[58] Field of Search ............................... 424/93; 47/58

[56] References Cited

U.S. PATENT DOCUMENTS

| 970,375 | 9/1910 | Hoskins | 47/57.5 UX |
| 1,999,458 | 4/1935 | Hollister | 47/57.5 |
| 2,923,039 | 2/1960 | Imus | 21/73 |
| 3,249,492 | 5/1966 | Lund | 435/32 |
| 3,249,493 | 5/1966 | Lund | 435/32 |
| 3,249,494 | 5/1966 | Lund | 424/93 |
| 3,255,095 | 6/1966 | Ricard | 435/32 |
| 3,280,504 | 10/1966 | Laing | 47/57.5 |
| 3,304,655 | 2/1967 | Mauget | 47/57.5 |
| 3,337,395 | 8/1967 | Page | 424/93 |
| 3,424,655 | 1/1969 | Ricard | 435/289 |
| 3,506,759 | 4/1970 | Ricard | 424/93 |

FOREIGN PATENT DOCUMENTS

| 866776 | 3/1971 | Canada . |
| 1577229 | 8/1969 | France . |

OTHER PUBLICATIONS

Docea et al., Analele Institutu lui de Cercetari pentres Protectia Plantelor (1972); Pube (1974), vol. 10, pp. 191–201.
Deal et al., Phytophathology (1972), vol. 62, No. 3, pp. 503–507.
Morquor et al., Acad. Sui Paris, Ser. D. 264(15) 1840–1843 (1967).
Dubos et al., Plant Disease Reporter, 1974, vol. 58, No. 10.
Isarlishvili et al. Trudy Nauchno–Iisledovatel'skaso Institute Zashchity Rastinii Gruz SSR (1975) pp. 133–136.
Dubos, Compt. Rend. des Seances Acad d'Agric de France, 64(14):1159–1168 (1978).
Chemical Abstracts, 67:42554a; 28:28397(2; 29:1457(4); 29:3099(5); 31:4042(8); 33:9351(4); 37:6697(9); 39:5283(9); 45:10463(a); 47:89621(d); 48:2299(b); 49:15146(g); 51:8878(f); 54:16713(d); 57:5117(d); 60:16440(g); 67:4254(O); 72:2484(w); 72:3105874; 76:42576(s); 77:98569(e); 79:89413(p); 79:113926(f); 84:54648(v); 85:145111; 89:8569(m).
Gorlenko, Mycology and Phytopathology 3(3) 203–206 (1969).
Grosclaude et al., Plant Disease Reporter, vol. 58, pp. 71–74.
Ricard, IWS Journal, vol. 7, No. 4, (Nov. 1976).
Grosclaude, Pers. Am. Phytopathol 2:507–516.
Ricard et al., Canadian Journal of Botany, vol. 46, pp. 643–647.
Ricard, PHD Thesis submitted to Oregon State University in 1966.
J. L. Ricard et al., Forest Products Journal, vol. 19, (8) p. 41.
Ricard (1970), Stvd. Forestalia Suecia No. 84.
Chemical Abstracts vol. 67:42555u (1967).
Grosclaude et al., Plant Disease Reporter, vol. 57, pp. 22–28.
Komatsu 1968, Trichoderma Viride as an Antagonist of the Wood-Inhibiting 11 Eymenomycetis, Rep. Tottori Mycol. Inst. 6:29–42.
Shields et al. 1963, Effect of a Mold, Trichoderma Viride, on Decay of Birch by Four Storage-Rot Fungi for Prod., Jour. 13(7):262.
DeTrogoff et al., Plant Disease Reporter, 60:677–680 (Aug. 1976).
Chidester, M. S. 1942, The Effect of a Mold, Trichoderma Lignorum, on Loblolly Pine Sapwood, A Wood Preserver Assoc. 38th Ann. Med. Rep.

(List continued on next page.)

Primary Examiner—Ronald W. Griffin
Attorney, Agent, or Firm—Brumbaugh, Graves, Donohue & Raymond

[57] ABSTRACT

This invention relates to a method of controlling soil-borne pathogens in plants by:
(a) growing a viable culture of one or more microorganisms antagonistic with respect to the soil-borne pathogens to be controlled said microorganism being selected from the group consisting of Trichoderma or Scytalidium;
(b) drying the entire culture;
(c) grinding the viable dried culture to form an admixture containing propagules, metabolites and partially digested growth medium; and
(d) treating the plants with the admixture which enables the microorganisms to grow internally within the plant.

29 Claims, No Drawings

OTHER PUBLICATIONS

Gindrat et al., vol, 60, No. 4, Plant Disease Reporter, Apr. 1976, pp. 321–325.

Garrett, S. D. Toward Bal. Control of Soil–Borne Plant Pathogens.

M. K. Baker et al., Ecology of Soil Borne Plant Pathogens, U. Calif. Press, pp. 4–17.

Wendling, R., 1932, Trichoderma Lignorum as a Parasite of Other Soil Fungi, Phytopathology, 22, pp. 837–845.

Hyppel, A., 1963, The Influence of Temperature on the Antagonistic Effect of Trichoderma Viride and Fomes Annosus Cke. Studio Forestala Succica 4.

Manka, K., 1965, Saprophytic Soil Fungi as a Factor for Determining the Development of Phytophathogenic Fungi Bring in the Oil, Wyzaza Szkola Rolincya, Posnon.

METHOD OF USING IMMUNIZING COMMENSALS

This application is a continuation of application Ser. No. 269,765, filed on June 3, 1981, now abandoned, which is a continuation-in-part of my co-pending application Ser. No. 76,061 filed 9/17/79 now abandoned which in turn, was a continuation-in-part of my application Ser. No. 883,272 filed Mar. 3, 1978, now abandoned. That application is a continuation-in-part of my application Ser. No. 722,767 filed Sept. 13, 1976, now abandoned, which, in turn, is a continuation-in-part of my application Ser. No. 593,355 filed July 7, 1975, now abandoned, which, in turn, is a continuation-in-part of my application Ser. No. 489,874 filed July 18, 1974, now abandoned which, in turn, is a continuation of my application Ser. No. 32,281, filed Apr. 27, 1970, now abandoned.

BACKGROUND OF THE INVENTION

The search for biological control methods has taken increasing importance in recent years. Substitutes are needed for established methods involving the use of esoteric chemicals with troublesome lingering residues as described in Rachael Carson's *Silent Spring*. Another goal of biological control is to provide economically feasible solutions to certain problems such as the damage caused by *Fomes annosus*, disease fungus attacking many forest tree species, or the damage caused by *Ceratocystis ulmi* to elm trees and by Botrytis to grapes.

In the investigation of biological control methods, many attempts have been made at manipulating the microbial population of the rhizosphere and other components of the external environment of plants, particularly in the soil. Most of these attempts failed, often because of the extreme diversity of chemical and biological factors present in such a system, resulting in great "buffer" capacity. A few instances of noticeable successes were obtained, as in the control of Phymatotrichum root rot of cottom, Ophiobolus root rot of wheat, Streptomyces scab of potato, Fusarium root rot of bean, Sclerotium stem rot of peanut, and a Fomes root rot of the rubber tree in Malaya.

The present inventor has discovered a new approach to biological control, namely the utilization of microbial immunizing commensals. The concept was reduced to practice under actual field conditions demonstrating its effectiveness in terms of the traditional cirteria for cause-to-effect relationships in microbiology and related fields, the postulates of Koch.

Immunizing commensals are microorganisms which can exist in the internal environment in contrast with the external environment or surroundings, soil for example, of higher plants and animals or other substrates. They grow internally of the plant or other host to be protected without causing damage to it, and at the same time establish a population of an immunizing commensal which controls or eliminates undesired pathogens. Occurrence of these microorganisms provides protection to their host against certain harmful microorganisms.

This concept and numerous specific techniques for carrying it out are fully described in the present inventor's co-pending U.S. patent application Ser. No. 883,272, which is herein incorporated by reference. Prior patents issued or applied for in this and related areas include U.S. Pat. Nos. 3,255,905 and 3,424,655, to Jacques L. Ricard, the inventor in the instant application; U.S. Patent Application "Wood Protection Process and Antibiotic" by Jacques L. Ricard and Walter B. Bollen, filed in January, 1967; U.S. Patent Application "Immunizing Commensals Utilization Method," filed by the same Jacques L. Ricard in June, 1967; French patent application Ser. No. 119,895 for a process of obtaining microbial commensals and for their utilization to combat microbes, insects and other organisms harmful to plants, animals and man, and products of the process; and a U.S. Patent Application for "Extruded Bark Pellet," filed by the same Jacques L. Ricard and Raymond A. Currier on Feb. 10, 1969.

BRIEF SUMMARY OF THE INVENTION

The present invention relates to specific applications of the aforementioned discovery, in which immunizing commensals are based on Scytalidium sp. or Trichoderma sp. The commensals are prepared by inoculating grain with the microorganism, incubating the mixture, and then recovering spores of the microorganism. The present invention may be used, inter alia, to control soil-borne pathogens such as *Phomopsis viticola*, Armillaria, Fusarium, *Phomopsis sclerotioides*, *Phoma beta*, and Pythium as well as the pathogen causing onion smut. Other pathogens to which Scytalidium or Trichoderma are antagonistic, can also be controlled, as will be hereinafter described.

In connection with the speciation of Trichoderma, it should be noted that Trichoderma is one of the most common soil fungi the world over, and has been studied on and off since the 1930's. It has never been found to accumulate in the environment for any length of time, in spite of determined efforts to do so, because the normal population of Trichoderma is held in check by naturally occurring predators. The classification of Trichoderma species has been the subject of scientific debate for a number of years. Bisby and Rifai represent two distinct viewpoints. The former argues that only the genus Trichoderma is significant (since the various "species" appear to mutate from one to another), and lumps all of the species under *Trichoderma viride*; Rifai claims that there are more or less distinct specie "aggregates" under the genus Trichoderma. The correctness of either view depends on the culture medium used. Under laboratory conditions, using artificial or semi-natural culture media, Rifai's aggregates are relatively stable. Under natural conditions they are not, and Bisby's viewpoint is more realistic.

A method of counteracting and controlling the harmful effects of *Phomopsis viticola* and Botrytis in grapes; of *Ceratocystis ulmi* in elm trees; of Fusarium in pink; of *Phomopsis sclerotioides* in cucumbers; of Armillaria and *Fomes annosus* in spruce and forest pine; of Armillaria (rot) in grapes and fruit trees; of *Lentinus lepideus* in pine poles, such as utility poles; of smut in onion beds; of *Phoma beta* and *Pythium ultimum* in sugar beet seeds; and of Stereum, Ceratocystis, Poria, and Verticillium, comprises administering an effective amount of the commensal to the afflicted plant in a suitable manner. As described below, the immunizing commensal may be administered to trees as pellets inserted into the trunk of the tree. The immunizing commensal may also be administered to plants as a powder, a spray, or as a tablet.

The mixture in which the immunizing commensal is administered should contain nutrients and protective metabolites which allow the immunizing commensals to become established in the host to be protected. Most conveniently such a mixture may be obtained by culturing the immunizing commensal on a solid substrate, such as grains. After the cultured immunizing commensal has reached a suitable level of growth, the solid substrate is then pulverized to prepare a powder. In the case of an organism such as Trichoderma or Scytalidium, the powder typically will contain at least $10^6$ spores of grams dry weight. The partially digested growth medium which becomes an inherent part of this substrate provides the requisite nutrient, while the metabolites which resulted from culturing, and which remain in the powder, provide a protective environment for the beneficial organism.

Generally, it has been found that Trichoderma exhibit antagonism to the foregoing organisms. However, some are more effective than others, the effectiveness depending on climatic conditions, and the organism to be controlled. For specific applications the techniques of identifying and culturing the optimum strain involving established cross-plating procedures, are well described in the publications and patents identified above, particularly my U.S. patent application Ser. No. 883,272 filed March 3, 1978. Preferred organisms are *Scytalidium lignicola* ATCC 16,675, *Trichoderma polysporum Rifai* ATCC 20,475 *Trichoderma viride sensu Bisby* ATCC 20,476 and *Trichoderma viride sensu Bisby*, Strain CG/BINAB-INRA 1 030 (Pasteur Institute).

Mixtures of these organisms, particularly mixtures of Trichoderma strains, are frequently desirable to provide finished products effective over a range of conditions. For example, at lower temperature, i.e., below about 10° C., *Trichoderma polysporum* is frequently more effective than *Trichoderma viride*. At higher temperature, the converse is true.

DETAILED DESCRIPTION OF THE INVENTION

In accordance with the present invention, immunizing commensals of Scytalidium or Trichoderma containing at least $50 \times 10^6$ spores/gram, dry basis, are applied to plants as follows to treat the following afflictions of plants:
treating pink to control Fusarium;
treating cucumber to control *Phomopsis sclerotioides;*
treating seeds of spruce and forest pine to control Armillaria and *Fomes annosus;*
treating grapevines and fruit trees against Armillaria (rot);
treating elm trees against *Ceratocystis ulmi;*
treating wooden poles, e.g., pine poles, to control *Lentinus lepideus;*
treating onion seeds to control smut;
coating sugar beet seeds to control *Phoma beta* and *Pythium ultimum;*
treating grapes to control Botrytis and *Phomopsis viticola;*
control of conifer rust with Scytalidium; and
treating Stereum, Ceratocystis, Poria, and Verticillium.

In particular, the immunizing commensal can be based on *Trichoderma viride* or *Trichoderma polysporum*. Most preferably the immunizing commensal is based on *Scytalidium lignicola* ATCC 16,675, *Trichoderma polysporum Rifai* ATCC 20,475, *Trichoderma viride sensu Bisby* ATCC 20,476, or *Trichoderma viride sensu Bisby* strain CG/BINAB-INRA 1 030 (Pasteur Institute).

The immunizing agent can be applied in the following forms:

As a concentrate, it can be sprayed onto fruit trees, mushroom soil beds, and grapevines, and for wetting beds of flowers, grapevines, and potatoes, and cucumber.

Tablets for flowers, seed beds, nurseries, mature trees, and wooden telephone and telegraph poles can be prepared.

As pellets, it may be spread on or incorporated into compost, soil treated with fumigants, or various seeds.

As a powder it may be spread on or mixed with seeds.

In each case, the immunizing commensal is applied in an amount effective to control target pathogens, typically in conjunction with partially digested growth medium and the metabolites resulting from culturing, and the application is repeated, if necessary, to maintain an effective level of immunizing commensal. For some applications of the present invention, one application per growing season should be sufficient to develop the required protective population of immunizing commensal. In treatment of trees, such as the treatment of Dutch elm disease, or controlling decay in pine poles, a population of an immunizing commensal, once established, can be effective for many reasons.

Preparation of the immunizing commensals is illustrated in the following example:

EXAMPLE I

About 250 g. of cracked barley and 250 g. of rice are introduced into sacks of a thermostable plastic material along with 14 ml. of a solution of 0.4% $CuSO_4.5H_2O$, and 400 ml. of an aqueous solution of 0.5 M $CH_3COOH$ and 0.5 M sodium acetate. The sack is closed and plugged with a ball of cotton in the opening, and autoclaved for two hours at 121° C. After cooling, the sack is inoculated with, e.g., *T. viride* ATCC 20, 476. The sack is then incubated at 20°–22° C. for 10 days under ordinary light, and mixed gently as necessary to obtain uniform sporulation (shown by the appearance of green conidia) throughout the substrate. Two treatment methods can then be applied to the contents of the sack:

A. Preparation of Trichoderma Powder

The contents are dried at 45° C. in a current of warm air. When the moisture is below 20% by weight, the product is ground in a hammer mill equipped with a 0.6 mm screen. The resulting powder can contain up to $10 \times 10^9$ spores/gram, and in particular $50 \times 10^6$ to $10 \times 10^9$ spores/gram. It will also contain metabolites resulting from culturing Trichoderma and partially digested growth medium. The spores are counted microscopically following the technique described by Gindrat and Ricard ("Technique for Counting Conidies of *Trichoderma viride* Dispersed in Inoculants Based on Barley Flour," Plant Disease Reporter 1976-60 pp. 321–325).

One can mix the powder with water conditioning agents and use it as a spray for controlling fungal diseases to fruit trees such as Armillaria, among other uses for the spray. Alternately, the powder can be formed into pellets without additives, for inoculation of trees or poles susceptible to attack by Stereum, Ceratocystis, Lentinus, or Poria spp. In a third use, the powder can be mixed with fresh or composted bark, with or without peat, as a substrate in which to grow seedlings in greenhouses or nurseries, or container-grown plants, susceptible to attack by plant pathogens such as Phomopsis, Pythium, Verticillium or Fusarium spp. In a fourth type of application, the powder can be added to standard seed pelleting components for the control of, for example, *Phoma beta* or Pythium in germinating sugar beet seeds.

B. Preparation of "Pure" Spores of Trichoderma and Feed for Animals

One and a half liters of water is acidified (with lactic acid, citric acid, sulfuric acid, etc.) and buffered to a pH of about 4.0, but definitely less than 4.5 in order to avoid significant bacterial contamination, particularly by Enterobacteria. The acidified water is added to the sack, and the sack is mechanically shaken for 30 minutes. The contents are then passed through a screen, yielding a suspension of dark green spores and grain impregnated with mycelium.

The grain is dried, producing a food for animals which is rich in amino acids, as a result of the proliferation of the fungus which converts cheap nitrogen, derived for example, for ammonium salts, into hyphal cell components including amino acids.

The suspension of spores is centrifuged, dried, and ground, yielding a powder of spores containing more than $1 \times 10^9$ spores/grams and up to $30 \times 10^9$ spores/grams, and often between 25 and $30 \times 10^9$ spores/grams. These spores possess Van der Waals forces characteristic of micro-particles, and thus constitute an excellent mycofungicidal product as a spray without any additives. When particular restrictions require it, the preparation can be sterilized by gas or by heat, because the dead spores in sufficient concentration still exert a mycofungicidal activity, probably through the action of enzymes immobilized on their surfaces.

If grain saturated with immunizing commensal, especially with Trichoderma, is dried and ground as indicated above, the resulting concentration of at least $50 \times 10^6$ spores/grams may be sufficient for a large number of applications. It has been ascertained that certain other applications, in particular for the treatment of Botrytis in grapes, require a concentration on the order of $15 \times 10^9$ spores/grams or more. On the other hand, when the mycofungicide is to be used as a spray, the maximum dimension of the particles ought to be on the order of about 10 microns. Spores of Trichoderma are, in general, of a diameter on the order of 3 microns, but the aforementioned powder often contains particles exceeding 10 microns in size (sometimes as much as 20% of the powder).

A mycofungicidal product corresponding to these requirements can be obtained by subjecting the spore-grain mixture to an extraction, either wet or dry, in order to eliminate a large part of the support and to obtain a more concentrated powder of spores.

In the dry extraction, the spores which coat the grain following incubation are dried, and then subjected to a shaking or rubbing operation, followed by a sifting step in which the concentrated powder of spores passes through the sieve and the grain remains atop the sieve. In the wet extraction, the paste of incubated grain which is formed when the incubated grain is agitated in the acidified water is sifted, yielding on the one hand a fine suspension of spores, and on the other hand grain impregnated by mycelium. The suspension of spores is centrifuged, dried, and ground to obtain the particular dimension desired. The dry mode of extraction is preferred. By either of the foregoing extraction processes, it is possible to obtain a powder of spores containing from $1 \times 10^9$ to $30 \times 10^9$ spores per gram, and generally between $25 \times 10^9$ and $30 \times 10^9$ spores per gram.

The grain impregnated with mycelium and enriched in amino acids, which constitutes the residue from the above sifting steps, is an excellent animal food. Toxicological tests carried out on this food have shown that it is less toxic than table salt, and thus presents practically no toxicity.

The treatment of elm trees with immunizing commensals of Trichoderma is illustrated in the following example:

EXAMPLE II

One hundred forty-six diseased elm trees were selected. The trees were at least 20 to 80 cm in diameter. The seriousness of the disease was measured by the proportion of damaged foliage.

Seventy-eight trees inoculated by various means were compared with 47 control trees. The inoculations were effected with Trichoderma grown on cracked barley grain. The grain was ground to a flour containing at least $50 \times 10^6$ viable spores per gram, dry basis. The flour was compressed into pellets of about 3 mm in diameter and 20 mm in length, weighing at least 0.5 g each. Holes of an appropriate size were drilled or stamped in the trees at a convenient height for placing 5 to 20 pellets per tree, regularly spaced in a circle or a spiral. The inoculation was carried out in March or July. The results were observed in July of the following year by observing variations in the alteration undergone by the leaves.

Twenty-one trees were treated with pellets of bark in place of pellets of Trichoderma, to determine the ultimate effect of the mechanical contact.

Alterations undergone by the leaves increased for 40.4% of the control trees. An almost equal proportion was observed for the trees inoculated in March. Among those inoculated in July, the percentage of trees showing an increased change was 12.52%. Twelve of the trees "inoculated" with bark pellets, 57.1% of this group, showed an increase in alterations.

The selection of the time of treatment appears to be important for the control of disease with propagules of Trichoderma.

One can rely on these relations if the inoculants of Trichoderma acts by concentrating their metabolites in the vascular system of the tree. When the tree reacts rapidly to a mechanical lesion caused by the introduction of the Trichoderma granules, there occurs only a weak or no dispersion of the metabolites originating from the introduced fungus.

Whether the therapeutic effect of the pellets of Trichoderma is provoked directly by the extraction of the soluble metabolites in water, or indirectly by the growth of hypha or by the transport of conidia out of the pellets, there ought to be produced in the tree a certain distribution of the contents of the pellets. An immediate blockage of the capillaries at the places where the pellets are introduced would prevent the inoculation of Trichoderma from acting in the desired manner. It is known that the rates of these reactions vary at various points during the growth season.

The effectiveness of a mycofungicidal product derived from Trichoderma in accordance with the present invention in the treatment of grapes has been studied, and the results are presented in the following example:

EXAMPLE III

It has been established that the spores of *Trichoderma viride sensu Bisby* prepared in a powder in accordance with Example I(A), employed at a concentration of $10^8$/ml, have an effectiveness in the vicinity of 70% following the coefficient of Abbott.

The results of the study are set forth in Table I below:

TABLE I

Effectiveness of *Trichoderma viride* on Gray Rot caused by *Botrytis cinerea*

| Treatment | % Effectiveness Ground Gelatin | % Rot In Untreated Control |
|---|---|---|
| Natural Infection | 70 | 31 |
| Artificial Infection | 71 | 61 |

Four applications in each case, except control. Observations on the berries (method of Desaymard).

The active product was applied in the form of a preparation based on ground agar medium.

It has been ascertained that, when the concentrate of the invention containing spores of Trichoderma (Pasteur Institute 1030) is sprayed with a customary insecticidal, anti-mildew and anti-oidium treatment four times during the season, at the flower setting, at the formation of the grape, at ripening, and three weeks before the harvest, results are obtained which are generally sufficient to satisfy established biological norms. In effect, these norms establish:

(a) the average ratio of gray rot should be reduced to 50% of that of the untreated control.

(b) the maximum ratio of gray rot tolerated in the treated parcels is 20%. The present tests have shown 61% rot in the control and 71% effectiveness for the *Trichoderma viride* in the parcels which were artificially infected with Botrytis. In the parcels allowed to become naturally infected, the rot in the control was 31% and the *Trichoderma viride* showed 70% effectiveness.

A second series of studies was carried out with ground agar medium only and with ground agar medium plus a protective cover.

The results obtained in the second test are given in Table II below:

TABLE II

Effectiveness of *Trichoderma viride* Against Gray Rot caused by *Botrytis cinerea* in Grapes

| Treatment | % Effectiveness |
|---|---|
| Ground agar medium without cover | 54.8 |
| Ground agar medium with cover | 22.6 |
| Concentrate of the invention, without cover | 63.5 |
| Concentrate of the invention, with cover | 47.5 |
| Control with cover (% rot) | 16.5 |

Four applications in each case, except control.

The cover consisted of simultaneously applied insecticide (methomyl), anti-oidium (S) and anti-mildew (Cu) fungicides, and the Trichoderma.

The mycofungicidal product described in Example III was also studied in the treatment of grapes against excoriation caused by *Phomopsis viticola*. Tests have demonstrated that the product of the present invention has the same effectiveness as sodium arsenite when the control shows a 50% excoriation at the level of the first internode. The results are shown in Table III.

TABLE III

Effectiveness of *Trichoderma viride* Against Excoriation Caused by *Phomopsis viticola*

| Treatment | Notation of Excoriated Surfaces (method of Desaymard) |
|---|---|
| Ground agar medium | 82% effectiveness |
| Filtrate of Culture | 69% effectiveness |
| Sodium Arsenite, 1250 gm/hl | 91% effectiveness |
| Control, untreated | 57% of surfaces excoriated |

It has also been discovered that mycofungicidal concentrates as described above can be used advantageously for the preservation of citrus fruit and bananas. It is known that citrus fruit and bananas are stored usually at temperatures below 14° C. during several weeks, and sometimes several months before consumption. During that period, rot can develop on the fruit by infection with molds such as *Penicillium digitatum* or *italicum*, *Alternaria tenuis* or *Colletotrichum musae*. So that some of the fruit becomes unsuitable for consumption and it is necessary to find means to avoid this infection by molds. The applicant has now discovered that such molds are attached by the immunizing commensals of the type Trichoderma and Scytalidium.

I have discovered that treating citrus fruit and bananas with propagules, spores or metabolites of immunizing commensals, such as Trichoderma and/or Scytalidium will provide for surprising preservation of such fruits.

By the process of the invention, the development of molds is avoided during the storage period before consumption of the fruit and thus, in using products (immunizing commensals) which are totally innocuous for the environment and the consumer, offering thereby a major advantage on the chemical fungicides such as thiabendazole which is used commonly for that treatment and to which certain strains of pathogenic molds are becoming tolerant.

Immunizing commensals which may be used particularly are *Scytalidium lignicola* ATCC 16,675, *Trichoderma polysporum Rifai* ATCC 20,475, *Trichoderma viride sensu Bisby* ATCC 20,476 or *Trichoderma viride sensu Bisby* strain CG BINAB-INRA I 030 (Institute Pasteur).

To allow convenient application, the commensals are provided preferably as powdery concentrate of the type described above, in which propagules, spores or metabolites are dispersed in a vegetal flour.

In these powdery concentrates, the concentration of propagules, spores or metabolites can vary considerably and range more particularly from $5 \times 10^3$ to $4 \times 10^9$ spores, propagules or metabolites by gram of concentrate dry weight, the higher concentrations being preferable.

For use, the concentrates concerned are suspended advantageously in water containing from 0.5 to 3 kg of powdery concentrate for about 100 liters of water according to the concentration in spores, propagules or metabolites of the concentrate.

To facilitate the application to fruit, it is advantageous to add water soluble wax to the suspension water at the rate of 0.5 liter to 1.5 liter about per 100 liters of water.

To prepare a product suitable for treatment of citrus fruit or bananas, the water soluble wax is mixed first with the amount of water needed and then the immunizing commensals concentrate is added in desired quantity to the suspension obtained. After agitation, the suspension obtained can be sprayed on the fruit to be protected. If it is preferred, the fruit can be dipped as well in the suspension of immunizing commensals.

EXAMPLE IV

One liter of water soluble wax (CITRACHINE available from PROCIDA Inc.) is added to 100 liters of water. To that solution, 0.5 kg of concentrate containing about $1 \times 10^9$ spores per gram dry weight of *Trichoderma viride* ATCC 20,476. After agitation, a homogenous suspension is obtained which can be sprayed on about 1 ton of oranges. After one month of storage at 10° C., no mold growth is observed on the citrus fruit.

EXAMPLE V

A solution is prepared with 1 liter of CITRACHINE in 100 liters of water. To that solution 1 kg of concentrate containing about $8 \times 10^6$ spores per gram dry weight of *Scytalidium lignicola* ATCC 16,675 is added. After agitation, the suspension obtained is used for dipping about 1 ton of bananas. After six weeks of storage at 12° C., no mold growth is observed on the bananas treated.

EXAMPLE VI

To a solution with 1 liter of water soluble wax in 100 liters of water, 2 kg of a mixed concentrate with *Trichoderma polysporum* ATCC 20,475—*Scytalidium lignicola* ATCC 16,675 containing about $2 \times 10^5$ spores per gram dry weight. After agitation, the suspension is sprayed on about 1 ton of lemons and after two months of storage at about 10° C. no mold infection is observed.

I claim:

1. A method for controlling soil-borne pathogens in plants comprising treating said plants with a mixture containing a viable culture of Trichoderma together with the partially digested growth medium of the culture containing the propagules and metabolic products resulting from growth of the organism, which digested medium enables said Trichoderma to grow internally within the plant, said Trichoderma being present in the mixture at a concentration of at least $10^8$ spores/grams of the mixture and being antagonistic with respect to the soil-borne pathogens to be controlled.

2. The method according to claim 1, in which said Trichoderma are selected from the group consisting of *Trichoderma viride*, *Trichoderma polysporum* and mixtures thereof.

3. The method according to claim 1, in which said Trichoderma is selected from the group consisting of *Trichoderma polysporum Rifai* (ATCC 20,475), *Trichoderma viride sensu Bisby* (ATCC 20,476) and *Trichoderma viride sensu Bisby* strain CG/BINAB-INTRA 1 030 (Pasteur Institute) or mixtures thereof.

4. The method according to claim 3, wherein a water suspension of said mixture containing from about 0.5 to 3 kg per 100 liters of water is sprayed on the plant to be protected.

5. The method according to claim 1 for controlling *Phomopsis viticola* and Armillaria in grapevines, wherein said mixture is applied to a grapevine as a powder containing an active ingredient at least about $50 \times 10^8$ spores Trichoderma per gram dry weight.

6. The method of claim 5, in which the Trichoderma is selected from the group consisting of *Trichoderma viride*, *Trichoderma polysporum* and mixtures thereof.

7. The method of claim 5, in which the Trichoderma strain is selected from the group consisting of *Trichoderma polysporum Rifai* (ATCC 20,475), *Trichoderma viride sensu Bisby* (ATCC 20,476), *Trichoderma viride sensu Bisby* strain CG/BINAB-INRA 1 030 (Pasteur Institute), and mixtures thereof.

8. A method according to claim 5, wherein said organism is Trichoderma and said pathogen to be controlled in *Phomopsis viticola* in grapevines.

9. A method according to claim 5, wherein said pathogen to be controlled is *Phomopsis viticola* in grapevines.

10. The method according to claim 1 for controlling Fusarium in pink wherein said mixture is applied to pink as a powder or pellet containing at least $50 \times$ about $50 \times 10^6$ spores Trichoderma per gram, dry weight.

11. The method of claim 10 in which said Trichoderma is selected from the group consisting of *Trichoderma viride*, *Trichoderma polysporum* and mixtures thereof.

12. The method of claim 10, in which said Trichoderma is selected from the group consisting of *Trichoderma polysporum Rifai* (ATCC 20,475), *Trichoderma viride sensu Bisby* (ATCC 20,476), *Trichoderma viride sensu Bisby* (ATCC 20,476), *Trichoderma viride sensu Bisby* strain CG/BINAB-INRA 1 030 (Pasteur Institute) and mixtures thereof.

13. The method according to claim 1 for controlling *Phomopsis sclerotioides* in cucumbers wherein said mixture is applied to cucumbers as a powder or pellet containing at least $50 \times$ about $50 \times 10^6$ spores Trichoderma per gram, dry weight.

14. The method of claim 13, in which said Trichoderma is selected from the group consisting of *Trichoderma viride*, *Trichoderma polysporum* and mixtures thereof.

15. The method of claim 13, in which said Trichoderma is selected from the group consisting of *Trichoderma polysporum Rifai* (ATCC 20,475), *Trichoderma viride sensu Bisby* (ATCC 20,476), *Trichoderma viride sensu Bisby* strain CG/BINAB-INRA 1 030 (Pasteur Institute), and mixtures thereof.

16. The method according to claim 1 for controlling smut in onion wherein said mixture is applied to onions as a powder or pellet containing at least $50 \times$ about $5 \times 10^6$ spores Trichoderma per gram, dry weight.

17. The method of claim 16, in which said Trichoderma is selected from the group consisting of *Trichoderma viride*, *Trichoderma polysporum* and mixtures thereof.

18. The method of claim 16, in which said Trichoderma is selected from the group consisting of *Trichoderma polysporum Rifai* (ATCC 20,475), *Trichoderma viride sensu Bisby* (ATCC 20,476), *Trichoderma viride sensu Bisby* strain CG/BINAB-INRA 1 030 (Pasteur Institute), and mixtures thereof.

19. The method according to claim 1 for controlling Phomabeta and *Pythium ultimum* in sugar beet seed wherein said mixture is applied to the seeds as a powder or pellet containing $50 \times$ about $50 \times 10^6$ spores Trichoderma per gram, dry weight.

20. The method of claim 19, in which said Trichoderma is selected from the group consisting of *Tri-

*choderma viride, Trichoderma polysporum* and mixtures thereof.

21. The method of claim 19, in which said Trichoderma is selected from the group consisting of *Trichoderma polysporum Rifai* (ATCC 20,475), *Trichoderma viride sensu Bisby* (ATCC 20,476), *Trichoderma viride sensu Bisby* strain CG/BINAB-INRA 1 030 (Pasteur Institute), and mixtures thereof.

22. The method according to claim 1 for controlling Botrytis in grapevines, wherein said mixture is applied to a grapevine as a powder containing an active ingredient at least about $5 \times 10^6$ spores Trichoderma per gram, dry weight.

23. The method of claim 22, in which the mixture contains at least about $15 \times 10^9$ spores Trichoderma gram, dry weight.

24. The method of claim 22, in which the Trichoderma is selected from the group consisting of *Trichoderma viride, Trichoderma polysporum* and mixtures thereof.

25. The method of claim 22, in which the Trichoderma strain is selected from the group consisting of *Trichoderma polysporum Rifai* (ATCC 20,475), *Trichoderma viride sensu Bisby* (ATCC 20,476), *Trichoderma viride sensu Bisby* strain CG/BINAB-INRA 1 030 (Pasteur Institute), and mixtures thereof.

26. A method for controlling soil-borne pathogens in plants comprising treating said plants with a mixture containing a viable culture of Trichoderma together with the partially digested growth medium of the culture containing the propagules and metabolic products resulting from growth of the organism, which digested medium enables said Trichoderma to grow internally within the plant, said Trichoderma being antagonistic with respect to the soil-borne pathogens to be controlled.

27. A method for controlling soil-borne pathogens in plants comprising treating said plants with dry flour, pellets prepared from such a flour, or an aqueous suspension of such a flour, said flour containing a viable culture of Trichoderma which was cultivated on a growth medium convertible into a flour, together with the partially digested growth medium of the culture containing the propagules and metabolic products resulting from growth of the organism, which digested medium enables said Trichoderma to grow internally within the plant, said Trichoderma being antagonistic with respect to the soil-borne pathogens to be controlled.

28. A composition for controlling soil-borne pathogens in plants comprising a mixture containing a viable culture of Trichoderma together with the partially digested growth medium of the culture containing the propagules and metabolic products resulting from growth of the organism, which digested medium enables said Trichoderma to grow internally within the plant, said Trichoderma being antagonistic with respect to the soil-borne pathogens to be controlled, wherein said composition contains between $20 \times 10^6$ and $5 \times 10^9$ spores per gram of Trichoderma.

29. A composition according to claim 28 wherein the composition is ground to a flour.

* * * * *

UNITED STATES PATENT AND TRADEMARK OFFICE
CERTIFICATE OF CORRECTION

PATENT NO. : 4,678,669
DATED : July 7, 1987
INVENTOR(S) : Ricard

It is certified that error appears in the above-identified patent and that said Letters Patent is hereby corrected as shown below:

Page 2, 6th line of 2nd col., "Phytophathogenic" should read --Phytopathogenic--;

Col. 1, line 29, before "disease" insert --a--;

Col. 1, line 41, "cottom" should read --cotton--;

Col. 1, line 49, "cirteria" should read --criteria--;

Col. 4, line 23, "reasons" should read --seasons--;

Col. 6, line 44, "acts" should read --act--;

Col. 8, line 29, "attached" should read --attacked--;

Col. 9, line 60, "INTRA" should read --INRA--;

Col. 10, line 14, "in" (1st occ.) should read --is--;

Col. 10, lines 29-30, delete ""Trichoderma viride sensu Bisby (ATCC 20,476),;

UNITED STATES PATENT AND TRADEMARK OFFICE
CERTIFICATE OF CORRECTION

PATENT NO. : 4,678,669
DATED : July 7, 1987
INVENTOR(S) : Ricard

It is certified that error appears in the above-identified patent and that said Letters Patent is hereby corrected as shown below:

Col. 10, line 51, "$5 \times 10^6$" should read --$50 \times 10^6$--; and

Col. 11, line 12, "$5 \times 10^6$" should read --$50 \times 10^6$--.

Signed and Sealed this

Second Day of February, 1988

Attest:

DONALD J. QUIGG

Attesting Officer        Commissioner of Patents and Trademarks